United States Patent [19]

Gluschenko et al.

[11] 4,286,060

[45] Aug. 25, 1981

[54] PROCESS FOR PRODUCTION OF AN AMINO ACID

[76] Inventors: Nina V. Gluschenko, Grazhdansky prospekt, 31, korpus 1, kv. 114, Leningrad; Vasily N. Bukin, Leninsky prospekt, 13, korpus 1, kv. 74, Moscow; Martin E. Beker, Zveyas, 4, Riga; Leonid V. Dmitrenko, prospekt Morisa Toreza, 9, kv. 393; Varvara A. Utenkova, ulitsa Matrosa Zheleznyaka, 51, kv. 70, both of Leningrad; Mariya A. Kuzmina, Leningradskaya oblast, ulitsa 1 Maya, 3, kv. 31, Sestroretsk; Lidia S. Kutseva, Moskovskaya oblast, ulitsa Svobody, 8, Malakhovka; Natalia M. Bazdyreva, ulitsa Usievicha, 25, korpus 3, kv. 407, Moscow; Gunar K. Liepinsh, Fr. Gailya, 13, kv. 2; Eleonora B. Trusle, Lielgabalu, 2, kv. 25, both of Riga; Tamara A. Pavlova, prospekt Shvernika, 16, kv. 69, Leningrad, all of U.S.S.R.

[21] Appl. No.: 31,754

[22] Filed: Apr. 20, 1979

[51] Int. Cl.³ .................... C12P 13/14; C12P 13/08; C12P 13/04

[52] U.S. Cl. .................... 435/110; 435/106; 435/115

[58] Field of Search ................ 435/106–116, 435/252

[56] References Cited

U.S. PATENT DOCUMENTS 2,431,163   11/1947   Boehm et al. .................... 435/252

*Primary Examiner*—Lionel M. Shapiro
*Attorney, Agent, or Firm*—Lackenbach, Lilling & Siegel

[57] ABSTRACT

The process according to the invention comprises submerged cultivation of microorganisms producing an amino acid in a nutrient media including nitrogen, mineral salts and a source of carbon - a mixture of hexose and pentose monosaccharides obtained by percolation hydrolysis of cellulose-containing plant raw materials, purified to remove furfural and containing oxymethyl furfural and lignogummin substances in an amount of 1–3% by weight of the monosaccharides.

The advantage of the process according to the invention resides in the abundance and low cost of the carbon source, reduction of the number of production steps, the presence of a mixture of monosaccharides stimulating the growth of microorganisms in the solution and improvement of quality of the end product.

6 Claims, No Drawings

PROCESS FOR PRODUCTION OF AN AMINO ACID

The invention relates to the microbiological industry, and more particularly to a process for production of an amino acid to be used in medicine, manufacture of synthetic fibers, food industry and animal husbandry.

Known in the art are processes for production of amino acids by submerged cultivation of nutrient media containing, as a source of carbon, hydrocarbons and their derivatives, such as n-paraffins $C_{11}$–$C_{18}$, cyclohexane, petroleum benzene, ethyl and methyl alcohols, acetic acid, carbohydrates, such as molasses, hydrolyzates of starch, potato or cereals, hexose hydrolyzates of selective species of plant raw material.

There is known a process for production of amino acids using a carbon hydride medium. The process comprises cultivating a mixture of microorganisms Micrococcus glutamicus in the presence of Arthobacter paraffineus or Brevibacterium ketoglutamicum which are capable of assimilating hydrocarbons and producing L-glutamic acid, L-lysine, L-valine and L-homoserine. (French Pat. No. 1577264).

Also known is a process for production of an amino acid by cultivating Pseudomonas, Corynebacterium or Saccharomyces in a nutrient medium containing unsaturated hydrocarbons as a source of carbon, mineral salts and growth stimulators. As a result of fermentation, 3.5 g of L-asparagine are obtained from 15.1 of nutrient medium. (Japanese Pat. No. 50-11472).

It is known to prepare L-lysine by cultivating strains of Brevibacterium ketoglutamicum 2473-Np-107 ATSS 21297 and Arthobacter paraffineus 2411-Np-82-ATSS 21298 in a nutrient medium containing, as a source of carbon, n-paraffins $C_{10}$- - $C_{50}$, aromatic hydrocarbons, petroleum fractions, crude oil. 3.2 mg/ml of lysine accumulate in a medium containing 5% by weight n-paraffins $C_{12}$–$C_{17}$(USSR Pat. No. 415890).

Another process is known for production of the amino acids L-lysine, L-asparaginic acid, L-alanine, L-valine, L-leucine and L-arginine by fermentation in a culture medium containing a source of carbon methanol. Concentration of methanol in the medium is below 3% by volume. As a source of nitrogen, use is made of ammonium salts, ammonia, urea, peptone or a yeast extract. Mineral components are added to the medium. The producer is a strain of Protaminobacter thiaminophagus ATSS 21927. The yield of the end products is as follows: L-lysine—0.21 g/l; L-asparaginic acid—0.14 g/l; L-alanine—0.48 g/l; L-valine—0.6 g/l; L-leucine—0.72 g/l; L-arginine—0.49 g/l (U.S. Pat. No. 3907641).

Known in the art is a process for production of L-glutamic acid by the method of microbiological synthesis using, as a source of carbons crude sugar containing saccharide materials, such as hydrolyzates of potato starch, or ground cereal grains, crude sugar syrup, beet molasses and cane molasses. The process comprises purification of said carbon sources from excessive biotin by microbiological methods, sterilization of surgar-containing saccharide material after purification by fermentation, cultivation of a glutamic acid producer and isolation of the end product. Maximum yield of glutamic acid is 39.2 g/l with the content of carbohydrates in the nutrient medium being 10%. As producers the following microorganisms are used: Micrococcus glutamicus, Bacillus subtilis, Brevibacterium lactofermentum and others (U.S. Pat. No. 3451891).

It is known to produce L-lysine in a culture medium containing hydrolyzate of polyasscharides as a source of carbon. The hydrolyzate of polysaccharides is not specified but it is known that polysaccharides occur in the cell wall of both plant materials and living organisms, such as yeast and fungi (cf. USSR Inventor's Certificate No. 171,727).

Known in the art is a process for production of L-lysine involving the use as raw material of hexose hydrolyzates of cotton seed lint or cellolignin of softwood. The process is conducted using producer bacteria Micrococcus or Brevibacterium. The yield of lysine is 25 g/l with the use of 12% sugar by weight of cotton seed lint hydrolyzate (USSR Inventor's Certificate No. 262053).

Cotton seed lint hydrolyzate and hexose hydrolyzates of cellolignin of softwoods contain six-atom monosaccharides. The absence of pentose monosaccharides adversely affects the process of microbiological synthesis.

This process has not been commercialized because cotton seed lint can be used for feeding animals after an unsubstantial treatment, and hexose hydrolyzates of cellolignin of softwood cannot be employed without additional treatment since hydrolyzates of plant raw material, apart from monosaccharides, contain impurities inhibiting the growth of microorganisms.

The above-described processes for the production of amino acids have a number of disadvantages:

low yield of end products when using petroleum hydrocarbons as a source of carbon nutrition;

the use of highly demanded raw materials—molasses, starch and the like which are used for feeding cattle;

complicated process of microbiological purification of carbohydrate raw material to remove biotin in case of production of L-glutamic acid.

It is an object of the invention to intensify the process.

Another object of the invention is to improve the quality and increase the yield of amino acid.

These objects are accomplished by a process for production of an amino acid comprising submerged cultivation of microorganisms producing the same in a nutrient medium including nitrogen, mineral salts, and a source of carbon—a mixture of hexose and pentose monosaccharides obtained by percolation hydrolysis of a cellulose-containing plant material, which is purified to remove furfural and contains oxymethyl furfural and lignogummin substances in an amount of 1-3% by weight of monosaccharides.

The advantage of using a mixture of monosaccharides obtained by percolation hydrolysis of a cellulose-containing plant raw materials is that the presence of pentose monosacchrides stimulates the growth of microorganisms and their producing capacity.

The removal of furfural, oxymethyl furfural and lignogummin substances contributes to an intensification of the process of microbiological synthesis of amino acid.

For more complete removal of the above impurities, the mixture of hexose and pentose monosaccharides is preferably purified by filtering at pH 3.3–3.7, evaporating in vacuum at 60°–80° C. to a content of monosaccharides of 6–11% by weight, oxidizing with an oxygen-containing gas in the presence of an adsorbent and an alkali, and sterilizing.

To improve the yield and quality of the end product, a mixture of hexose and pentose monosaccharides obtained by percolation hydrolysis of hardwoods and softwoods is preferably used.

The process for production of an amino acid according to the invention is carried out in the following manner.

The process for production of an amino acid involves the use, as a source of carbon, of a purified mixture of hexose and pentose monosaccharides obtained by percolation hydrolysis of cellulose-containing plant raw materials.

In the USSR plant raw material is processed by the method of percolation hydrolysis with diluted sulphuric acid. The percolation hydrolysis enables processing of all kinds of cellulose-containing plant raw material—rejects of agricultural production (rice and cotton husk, maize stump, sunflower seed husk and the like), rejects of woodworking and sawmilling (slabs, edgings, sawdust), and fuel wood, regardless of the species.

With two-stage hydrolysis, e.g. of hardwood, the process is conducted at the first stage with the formation, mainly, of pentose saccharides for subsequent production of furfural. At the second stage of the process, a solution of a mixture of monosaccharides is obtained having a ratio of monosaccharides which is preferred for microbiological synthesis of amino acid, namely 90–95% hexose monosaccharides and 5–10% pentose monosaccharides.

In processing softwood, hydrolyzates of the first stage contain a mixture of hexose (70–80%) and pentose (20–30%) monosaccharides. This mixture of monosaccharides is used for the production of albumin yeast. Hydrolyzates of the second stage of hydrolysis of softwood contain 95–98% of hexose and 2–5% of pentose monosaccharides.

Commercial hydrolyzates from percolation hydrolysis of cellulose-containing plant raw material contain a mixture of hexose and pentose monosaccharides in an amount of 2–3% by weight. By varying the percolation hydrolysis conditions and plant raw materials, solutions of a mixture of monosaccharides shown in the table below are prepared.

Apart from sugars, hydrolyzates of monosaccharides of plant raw materials also contain impurities representing a complex mixture of compounds differing in quantity and properties. The impurities of hydrolyzates may be divided into two groups: volatile and non-volatile components. The inhibiting volatile impurities amount to 1–3% by weight of the mixture of monosaccharides, and the content of inhibiting non-volatile impurities in the starting hydrolyzate is 5–6% by weight of the mixture of monosaccharides.

The presence of furfural in an amount of 0.03–0.07% by weight in the hydrolyzate of cellulose-containing plant raw materials intoxicates the fermentation system of microorganisms. The presence of oxymethyl furfural in the hydrolysis medium decelerates the growth of microorganisms and results in hampering their producing capacity. Lignogummin and dyeing substances which are present in hydrolyzates are sorbed in cell walls of microorganisms to hinder access of nutritive substances to the cell.

As the percolation hydrolysis of cellulose-containing plant raw material is conducted in the presence of sulphuric acid as the catalyst of the process, the resultant solution of a mixture of monosaccharides is initially neutralized.

Acid hydrolyzate is neutralized with milk of lime or ammonia liquor, preferably to pH 3.3–3.7 and filtered to remove the suspended matter.

The filtrate is evaporated in vacuum at 60°–80° C. to obtain a content of monosaccarides of 6–11% by weight which is an optimum condition for microbiological synthesis of amino acid.

Compliance with the above-mentioned conditions of the evaporation process not only permits the decomposition of sugars to be reduced, but also complete removal of inhibiting volatile impurities, namely, furfural and methyl furfural is thereby achieved.

Non-volatile organic impurities of the hydrolysate, such as oxymethyl furfural, lignogummin and dyeing substances are oxidized.

Oxidation of evaporated filtrate—mixture of monosaccharides is conducted with an oxygen-containing gas in the presence of an adsorbent (such as activated coal) or an alkali. Aeration is preferably performed for 60 minutes at 45° C.

TABLE

Composition of monosaccharides of hydrolyzates obtained by a percolation hydrolysis of a cellulose-containing plant raw materials

| Type of hydrolyzate | Cellulose-containing plant raw materials | Relative content of monosaccharides, % | | | | |
|---|---|---|---|---|---|---|
| 1 | 2 | glucose 3 | mannose 4 | galactose 5 | xylose 6 | arabinose 7 |
| Single-stage percolation hydrolysis | Softwood | 70.94 | 17.41 | 2.59 | 7.34 | 1.73 |
| | Hardwood | 61.93 | 2.78 | 1.61 | 32.36 | 1.31 |
| | Mixture of hard- and softwood | 66.57 | 10.17 | 2.03 | 19.77 | 1.45 |
| | Sunflower seed husk | 55.15 | 3.11 | 1.94 | 32.62 | 5.44 |
| | Maize stump | 49.49 | — | 2.72 | 43.43 | 4.79 |
| | Cotton husk | 61.22 | 1.46 | 1.30 | 36.42 | 1.30 |
| Second stage of two-stage percolation hydrolysis[x] | Softwood | 92.66 | 5.06 | — | 2.08 | — |
| | Hardwood | 92.87 | 1.84 | — | 5.29 | — |
| | Mixture of soft- and hardwood. | 92.75 | 3.62 | — | 3.62 | — |
| | Mixture of sunflower seed husk and maize stump | 90.30 | 1.95 | — | 7.77 | — |
| | Cotton husk | 92.82 | 2.39 | — | 4.79 | — |

[x]Hydrolyzates of the first stage of hydrolysis are used to obtain either furfural, or xylite, or fodder yeast.

In addition to oxidation of non-volatile impurities, the aeration accelerates coagulation of lignogummin substances which are in a colloidal state in the hydrolyzate.

The above-described steps enable lowering the content of oxymethyl furfural and lignogummin substances to 1-3% by weight of monosaccharides in the solution.

The purification according to the invention contributes to an intensification of the process of microbiological synthesis of an amino acid owing to the removal of inhibiting volatile and non-volatile impurities from the hydrolyzate.

A source of nitrogen and mineral salts are added to the purified solution of a mixture of monosaccharides, and the solution is then sterilized.

The resultant nutrient medium is inoculated with a 24-hour culture of a producing microorganism, and fermentation is conducted under aerobic conditions.

After the fermentation is over, the end product in the form of an amino acid is isolated by known methods.

The invention enables intensification of the process, improvement of the quality and yield of amino acid owing to the use as a source of carbon, of a mixture of hexose and pentose monosaccharides obtained by a percolation hydrolysis of cellulose-containing plant raw materials which are available in abundance.

Another advantage of the invention is the availability and low cost of the source of carbon since a mixture of monosaccharides obtained by percolation hydrolysis of a cellulose-containing plant raw material, such as wood, is 30% cheaper than the widely used source of carbon employed for the production of amino acid-molasses.

Besides, the use as a source of carbon of a mixture of monosaccharides permits the number of production steps to be dispensed with compared to the prior art process (cf. U.S. Pat. No. 3,451,891) which requires a complicated microbiological purification of the source of carbon—molasses to remove an excess of biotin.

A further advantage of the process according to the invention is that a solution of a mixture of monosaccharides used as a source of carbon also contains sufficient and optimum amounts of stimulators of growth of microorganisms, since cellulose-containing materials have a natural base.

The invention is also advantageous in that the use of a new source of carbon enables production, during the synthesis of amino acids, such as L-lysine in the form of a non-hydroscopic product which is not subject to caking during the storage.

A better understanding of the process for production of amino acid according to the invention may be had from reading the following examples.

EXAMPLE 1

A hydrolyzate obtained at the second stage of percolation hydrolysis of a mixture of soft- and hardwood, containing 2.51% hexose and 0.09% pentose monosaccharides was neutralized to pH 3.3, filtered and evaporated in vacuum at 60° C. to obtain a monosaccharide concentration of 6.0% by weight. The evaporated solution of the mixture of monosaccharides was oxidized with air oxygen for 60 minutes at 45° C. in the presence of activated charcoal, and filtered.

During the purification of the hydrolyzate, furfural was completely removed, which was established by gas chromatography. The content of oxymethyl furfural and lignogummin substances was 2.5% by weight of monosaccharides after the purification. The presence of these substances was tested by spectrophotometry of the hydrolyzate before and after the purification.

15 g of $(NH_4)_2SO_4$, 0.5 g of $K_2HPO_4$, 0.5 g of $KH_2PO_4$, 0.2 g of $MgSO_4\ 7H_2O$, 2.5 g of maize extract, and 0.4 g of homoserine were added to 1000 ml of the purified solution of monosaccharides, and the pH of the medium was brought to 7.0 with an alkali. The medium was poured in 50 ml batches into 750 ml rocking flasks. 0.5 g of chalk were added to each flask, and the medium was then sterilized at a gauge pressure of 0.8 atm for 30 minutes. Then 2.5 ml of a 24-hour culture of Brevibacterium 22 were added to each flask. The culture was prepared in a medium having the following composition: glucose—2% by weight; maize extract—2.0% by weight; NaCl—0.3% by weight; pH of the medium—7.0. The medium was sterilized, inoculated with the 24-hour culture from slant agar and cultivated during 24 hours at 28°-32° C. on a rocker.

A strain of Brevibacterium 22 short of homoserine was used as an L-lysine producer.

Fermentation was conducted at 28°-30° C. on a rocker performing at 200 r.p.m., for 60 hours. Concentration of L-lysine was 18 mg/ml, the yield of amino acid from the mixture of monosaccharides in the fermentation medium was 30%. The culture liquor was separated from the bacterial biomass, acidified to pH 4-5 and stabilized with sodium metabisulphite in an amount of 0.2% by weight. The stabilized liquor was passed through ion-exhange columns charged with ionites. The resultant eluate was evaporated to bring the content of L-lysine to 40% by weight, and the solution was acidified to a pH of about 5.0, cooled at 12°-14° C. and crystallized.

EXAMPLE 2

A hydrolyzate obtained at the second stage of percolation hydrolysis of softwood, containing 2.73% hexose and 0.07% pentose monosaccharides was neutralized to pH 3.5 and filtered, the filtrate was evaporated in vacuum at 70° C. to bring the content of monosaccharides to 11% by weight. The evaporated solution of monosaccharides was oxidized with air oxygen in the presence of activated charcoal during 30 minutes at 45° C. The solution was filtered. After the purification the solution of the mixture of monosaccharides did not contain furfural. This was tested by gas-liquid chromatography. The amount of oxymethyl furfural and lignogummin substances in the solution was 1% by weight of monosaccharides. Their presence was determined by spectrophotometry before and after the purification. 225 g of $(NH_4)_2SO_4$, 7.5 g of $K_2HPO_4$, 7.5 g of $KH_2PO_4$, 3 g of $MgSO_4.7H_2O$, 600 g of maize extract, 150 g of fodder yeast were added to 9.6 liters of the purified solution of the mixture of monosaccharides, and the volume was brought to 15 liters with water. The medium was charged into a 30 liter fermentation vessel and sterilized at a gauge pressure of 1 atm during 30 minutes. After the sterilization, the pH was brought to 7.0 with ammonia liquor. Then 750 ml of a 24-hour culture of Brevibacterium 22 prepared as described in Example 1 were added. Fermentation was conducted at 28°-30° C. with air purging at a rate of 1 cu.m per 1 cu.m of the medium and under stirring at 400-500 r.p.m. During fermentation, the pH of the medium was maintained with ammonia liquor or sulphuric acid. Fermentation time was 60 hours. The concentration of L-lysine was 22.4 g/l, the yield of amino acid was 32% by weight of the mixture of monosaccharides.

After the fermentation the culture liquor was acidified to pH 4–5 and stabilized with sodium metabisulphite in an amount of 0.2% by weight. The stabilized culture liquor was dried on a spray drier. The resultant product was non-hygroscopic, it did not agglutinate during storage and did not form lumps.

EXAMPLE 3

A hydrolyzate obtained at the second stage of percolation hydrolysis of hardwood, containing a mixture of 2.26% hexose and 0.14% pentose monosaccharides was neutralized to pH 3.7, filtered and evaporated in vacuum at 80° C. to bring the content of monosaccharides to 9% by weight. The evaporated solution of the mixture of monosaccharides was oxidized with air oxygen during 60 minutes at 45° C. in the presence of activated coal and filtered.

During the purification of the hydrolyzate, furfural was completely removed which was tested by gas-liquid chromatography. The content of oxymethyl furfural and lignogummin substances in the purified solution of the mixture of monosaccharides was 1.8% by weight of monosaccharides. Their presence was determined by spectrophotometry before and after the purification.

A source of nitrogen, mineral salts and growth stimulators were added to 660 ml of the purified solution of monosaccharides as described in Example 1, and the volume of the nutrient medium was brought to 1 liter with water. Fermentation was conducted in rocker flasks as described in Example 1. The content of L-lysine was 21.1 mg/ml, the yield of amino acid was 28% by weight of the mixture of monosaccharides.

EXAMPLE 4

A hydrolyzate from a single-stage hydrolysis of softwood, containing 2.55% hexose and 0.25% pentose monosaccharides was neutralized to pH 3.4, filtered and evaporated in vacuum at 75° C. to bring the content of monosaccharides to 10% by weight. The evaporated solution was oxidized with air oxygen in the presence of calcium hydroxide during 60 minutes at 45° C. The resultant precipitate was filtered off. Complete absence of furfural in the purified solution of monosaccharides was controlled by gas-liquid chromatography. The content of oxymethyl furfural and lignogummin substances was 1.8% by weight of monosaccharides. Their presence was determined by spectrophotometry.

25 g of $(NH_4)_2SO_4$, 0.5 g of $KH_2PO_4$, 0.5 g of $K_2HPO_4$, 0.4 g of $MgSO_4.7H_2O$ were added to 860 ml of the purified solution, and the volume was brought to 1 liter with water; pH of the medium was brought to 7.0 with ammonia liquor. The medium was poured into 750 ml rocking flasks in batches of 50 ml. 1 g of chalk was added to each flask, and the solution was sterilized at a gauge pressure of 0.8 atm for 30 minutes. The medium was inoculated with a 24-hour culture of *Brevibacterium flavum* ATSS 14067.

The medium for inoculating material had the following composition: (% by weight): glucose—2.0, maize extract—2.0, NaCl—0.3; pH—7.0–7.2; sterilization at a gauge pressure of 0.8 atm for 40 minutes. The above culture was incubated in rocking flasks at 28°–30° C. during 24 hours. The producing microorganism was *Brevibacterium flavum* ATSS 14067.

The main fermentation was conducted on a rocker at 28°–30° C. under stirring at 140 r.p.m. during 72 hours. Concentration of L-glutamic acid was 42 mg/ml, the yield of amino acid was 49% by weight of monosaccharides.

EXAMPLE 5

A hydrolyzate from the second stage of a two-stage percolation hydrolysis of hardwood, containing 2.23% hexose and 0.17% pentose monosaccharides was neutralized to pH 3.6, filtered and evaporated in vacuum at 72° C. to bring the concentration of monosaccharides to 10% by weight. The evaporated solution of the mixture of monosaccharides was oxidized with air oxygen during 30 minutes at 45° C. in the presence of activated coal and filtred.

Complete absence of furfural in the purified solution was tested by gas-liquid chromatography. The content of oxymethyl furfural and lignogummin substances in the purified solution of the mixture of monosaccharides was 2.2% by weight of monosaccharides. Their presence was determined by spectrophotometry of the solution before and after the purification.

450 g of $(NH_4)_2SO_4$, 7.5 g of $K_2HPO_4$, 7.5 g of $KH_2PO_4$ and 6 of $MgSO_4.7H_2O$ were added to 15 liters of the purified solution of monosaccharides.

The medium was charged into a 30 liter fermentation vessel and sterilized for 30 minutes at a gauge pressure of 1 atm. Then 750 ml of a 24-hour culture of *Brevibacterium flavum* ATSS 14067 were added.

The inoculating culture was prepared as described in Example 4. The main fermentation was conducted at 30°–32° C. under stirring at 200 r.p.m. and an air flow rate of 1 cu.m per 1 cu.m of the medium. The fermentation time was 56 hours, pH of the medium was maintained during the fermentation with ammonia liquor. The concentration of L-glutamic acid in the fermentation medium was 49.2 g/l, the yield of amino acid was 49.2% by weight of the mixture of monosaccharides.

EXAMPLE 6

A hydrolyzate of single-stage hydrolysis of a mixture of soft- and hardwood, containing 2.06% hexose and 0.54% pentose monosaccharides was neutralized to pH 3.5, filtered and evaporated in vacuum at 65° C. to bring the content of monosaccharides to 9.55% by weight. The evaporated mixture of monosaccharides was oxidized with air oxygen for 30 minutes at 45° C. in the presence of sodium hydroxide. The resultant precipitate was filtered off. After the purification, the solution of the mixture of monosaccharides did not contain furfural, which was tested by gas chromatography. The content of oxymethyl furfural and lignogummin substances in the purified solution was 3.0% by weight of monosaccharides, which was determined by spectrophotometry before and after the purification. 450 g of $(NH_4)_2SO_4$, 7.5 g of $K_2HPO_4$, 7.5 g of $KH_2PO_4$, 6 g of $MgSO_4.7H_2O$ were added to 12 liters of the purified solution of the mixture of monosaccharides, and the volume was brought to 15 liters with water. the prepared medium was charged into a 30 liter fermentation vessel and sterilized for 30 minutes at a gauge pressure of 1 atm. Then 750 ml of a 24-hour culture of *Micrococcus glutamicus* were added.

The inoculating culture was prepared as described in Example 4, but *Micrococcus glutamicus* was used as the producer.

The main fermentation was conducted at 28°–30° C. under stirring at 200 r.p.m. during 60 hours with air flow rate of 0.8 cu.m per 1 cu.m of the medium, and pH was maintained during fermentation with ammonia liquor. The concentration of L-glutamic acid in the culture liquor was 32.5 g/l, the yield of amino acid was 32.5% by weight of the mixture of monosaccharides.

What is claimed is:

1. A process for producing an amino acid, by means of submerged cultivation of an amino acid producing microorganism in a nutrient medium comprising nitrogen, mineral salts, and a mixture of hexose and pentose monosaccharides obtained by percolation hydrolysis of cellulose-containing plant raw materials, purified to remove substantially all furfural and containing oxymethyl furfural and lignogummin substances in an amount of 1–3% by weight of said monosaccharides.

2. A process according to claim 1, wherein the purification of said mixture of hexose and pentose monosaccharides is conducted by filtering at a pH of 3.3–3.7, and evaporating in a vacuum at 60°–80° C. to bring the content of said monosaccharides to 6–11% by weight, oxidizing and sterilizing said mixture.

3. A process according to claim 2, wherein oxidation is conducted with an oxygen-containing gas in the presence of an adsorbent or an alkali.

4. A process according to claim 1, wherein said hexose and pentose monosaccharides are obtained by percolation hydrolysis of materials selected from the group consisting of softwood and hardwoods.

5. A process according to claim 1, wherein said amino acid is L-lysine.

6. A process according to claim 1, wherein said amino acid is L-glutamic acid.

* * * * *